United States Patent [19]

Eggers et al.

[11] Patent Number: 5,713,856
[45] Date of Patent: Feb. 3, 1998

[54] MODULAR PATIENT CARE SYSTEM

[75] Inventors: Philip N. Eggers; Jeffery D. Schipper; Robert J. Duffy, all of Poway; Stephen J. Bollish, San Diego; Timothy W. Vanderveen, Poway; Derek K. Evans, San Diego, all of Calif.; Richard B. Kelsky, Pound Ridge, N.Y.

[73] Assignee: Alaris Medical Systems, Inc., San Diego, Calif.

[21] Appl. No.: 403,503

[22] Filed: Mar. 13, 1995

[51] Int. Cl.$^6$ ............................................. A61B 1/00
[52] U.S. Cl. ................................................ 604/65
[58] Field of Search ....................... 604/65, 49, 30–34, 604/50, 53, 66, 67, 118, 151, 246; 606/39, 42; 128/DIG. 12, DIG. 13

[56] References Cited

U.S. PATENT DOCUMENTS 4,529,401 7/1985 Leslie et al. ............................ 604/131
5,181,910 1/1993 Scanlon ................................... 604/67
5,527,289 6/1996 Foster et al. .

Primary Examiner—Manuel Mendez
Attorney, Agent, or Firm—Pennie & Edmonds LLP

[57] ABSTRACT

In accordance with the present invention, a modular patient care system provides patient monitoring and the supply of therapeutic requirements. Specifically, the system is comprised of an interface unit and a plurality of patient functional units. The interface unit provides an interface between the user and the system, and may be configured and adapted to provide different levels of functionality. Interface units with different levels of functionality may be interchanged so as to provide greater flexibility, safety, and cost effectiveness. Each interface unit contains interface ports for the transfer of information such as drug libraries, system configuration values, and event history. The functional units are internally programmed and controlled so as to provide a high level of system modularity, and require only power and interfacing functionality from the interface unit.

78 Claims, 17 Drawing Sheets

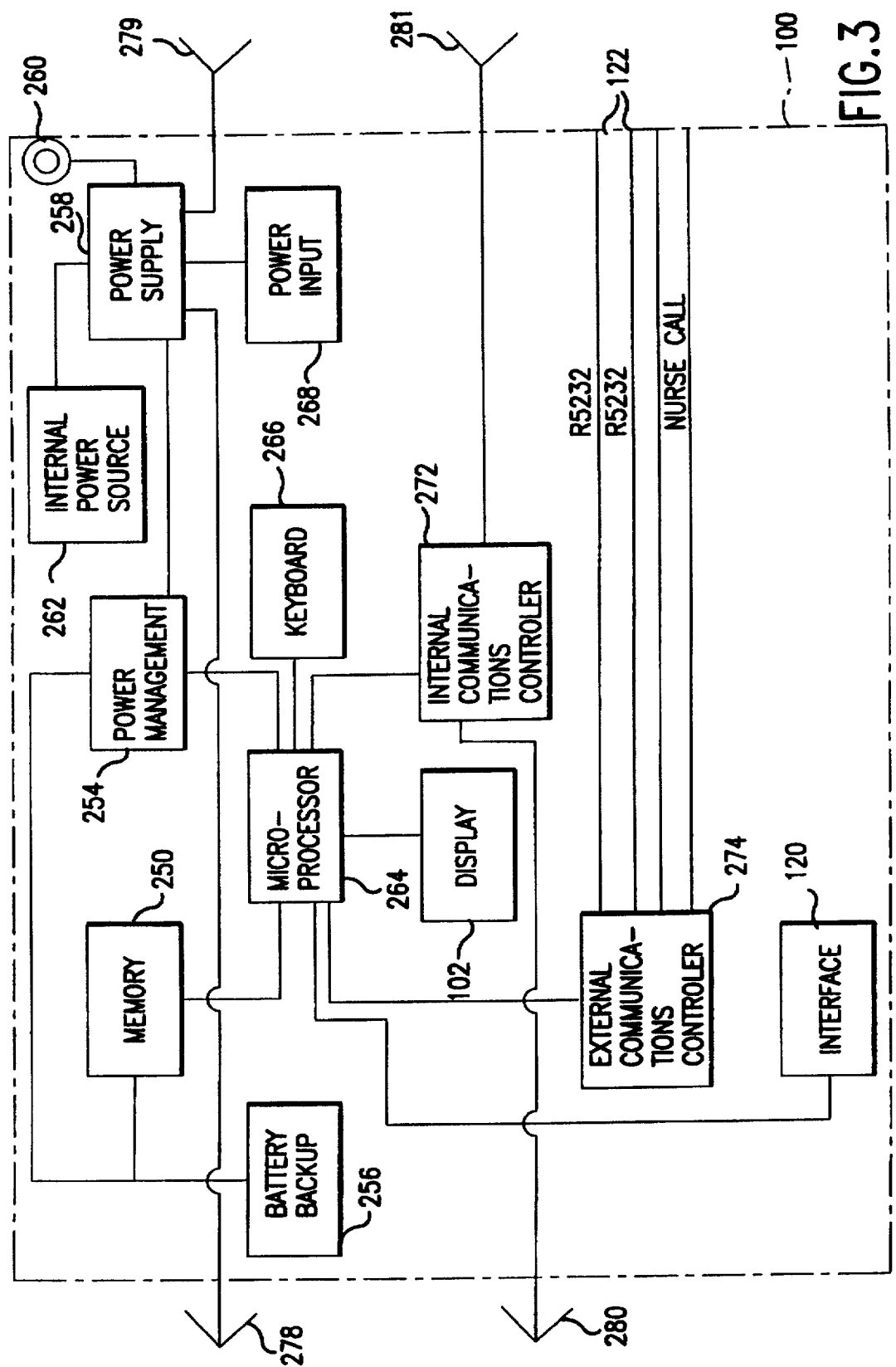

FIG. 8

INFUSION SETUP

RATE   40 ml/hr
VTBI   240 ml

>PRESS START

SECONDARY  START

FIG. 7

INFUSION SETUP

RATE   ___ ml/hr
VTBI   ___ ml

>SELECT RATE OR RECALL
PREVIOUS INFUSION

RECALL

INFUSION SETUP

| | | SEC 100 ml/hr 50 ml |
|---|---|---|
| RATE | PRI 40 | |
| VTBI | 240 | |

>PRESS START

[PRIMARY] [START]

INFUSION SETUP

RATE 40 ml/hr
VTBI 240 ml

>PRESS START

[SECONDARY] [START]

FIG. 11

MULTIDOSE 0800 hrs

RATE         100 ml/hr
VOLUME/DOSE   50 ml
DOSE INTERVAL EVERY 06 hrs
OF DOSES    04 DOSES
START TIME    09:00 hrs

>PRESS START                    START

FIG.14

MULTIDOSE 0800 hrs

RATE          ___0 ml/hr
VOLUME/DOSE   ........
DOSE INTERVAL ........
OF DOSES    ........
START TIME    ........

>ENTER RATE VALUE

FIG.13

MULTICHANNEL 0800 hrs

FLUSH
VTBI 40 ml
DURATION ___ min

ENTER FLUSH DURATION

MAINT-
ENANCE

FIG. 16

MULTICHANNEL 0800 hrs

MAINTENANCE
RATE ___0 ml/hr
VTBI ........
FLUSH NO

>ENTER MAINTENANCE
RATE VALUE

RECALL

FIG. 15

MULTICHANNEL 0800 hrs — 102

▣ MAINTENANCE/FLUSH

B   C   D 0 1 2 3 4 5 6 7 8 9 10 11 12
TIME (HRS)

>SELECT CHANNEL

MULTICHANNEL 0800 hrs — 102

▣ MAINTENANCE

RATE  100 ml/hr
VTBI  1000 ml
FLUSH 40 ml/20min

>PRESS ENTER TO
 CONTINUE

NEXT

DRUG CALCULATION

- DRUG AMOUNT: 0
- DILUENT VOLUME: ......
- PATIENT WEIGHT: ......
- TIME UNITS: ......
- DOSING UNITS: ......

mcg
mg
gram
unit
mEq

>ENTER AMOUNT OF DRUG IN CONTAINER

[DRUG LIBRARY]

FIG.22

DRUG CALCULATION

CONTINUOUS INFUSION

- RATE ___ ml/hr
- VTBI ___ ml
- DOSE ___ 0 mcg/kg/min

[CONC]: 1600 mcg/ml

>ENTER DOSE VALUE

[SETUP]  [BOLUS]

FIG.24

DRUG CALCULATION

BOLUS DOSE 100 mcg

DOSE

DURATION _ 5 min

RATE  6 ml/hr (VTBI=0.5ml)

[CONC]: 1600 mcg/ml

>PRESS START TO BEGIN INFUSING BOLUS DOSE

SETUP | CONTIN-UOUS | START

FIG.23

DRUG CALCULATION
GENERAL DRUG LIBRARY

A-D | E-I | J-M | N-R | S-Z

AMINOPHYLLINE 500 mg/250ml

BRETYLIUM 500 mg/250ml

DOBUTAMINE 500mg/250ml

DOPAMINE 400mg/250ml

DOPAMINE 800mg/250ml

>SELECT DRUG/CONCENTRATION

PAGE UP | PAGE DOWN

FIG.25

DRUG CALCULATION

BOLUS DOSE ___0 mcg
 mcg/kg
 mg
 mg/kg

DOSE
DURATION
RATE

[CONC]: 1600 mcg/ml

>ENTER BOLUS DOSE

SETUP | CONTIN-UOUS

A BOLUS VTBI=8.5 ml
B
C
D

MODULAR PATIENT CARE SYSTEM

BACKGROUND OF THE INVENTION

1. Technical Field

The present invention relates to a modular, programmable patient care system. Specifically, the present invention relates to a method and apparatus for centrally interfacing with a plurality of individually controlled functional units which provide patient monitoring and therapies.

2. Discussion of the Related Art

Systems containing multiple infusion pumping units and sensing devices such as blood pressure monitors and pulse oximeters are known in the medical field. For example, U.S. Pat. No. 4,756,706 to Kerns et al. discloses a centrally managed infusion pump system in which pump and monitoring modules are selectively attached to a central management unit. The central management unit controls the internal setup and programming of the attached modules, and receives and displays information from them. Each module is capable of being detached from the central management unit, and while detached is capable of operating independently of the management unit.

U.S. Pat. No. 4,898,578 to Rubalcaba, Jr. also discloses a drug infusion system which includes a plurality of infusion pump modules selectively attached to a central management unit so as to provide for centralized control. In particular, the central management unit obtains infusion parameters from the user and then performs calculations with the parameters to establish the desired infusion rate. Once this rate is determined, the central management unit may control the infusion accordingly.

In addition, U.S. Pat. No. 5,256,157 to Samiotes et al. discloses a programmable infusion pump for dispensing a drug in accordance with the requirements of a particular user. Specifically, the pump includes a microprocessor which communicates with a replaceable memory module so as to configure the pump to meet individual user needs.

However, these related art systems contain several disadvantages. For example, in these systems, the central management unit must be aware of and must control much of the functionality of the attached functional units. This is undesirable in that the system cannot be easily upgraded when a new type of functional module is to be added without replacing or modifying the central unit.

Moreover, these systems disclose a single complex central management unit that must be used to control and program the functional units. Complex central management units may be undesirable in clinical situations which do not require skilled professionals such as anesthesiologists to operate the patient care system, as they introduce a greater risk of error and confusion during use. Therefore, there is a need for less advanced central units which may be interchanged with the complex interface units depending on the clinical situation and the skill of the system operator.

A further problem with some related art systems is that they do not include interfaces between the central management unit and external devices so as to allow for the uploading or downloading of information such as new system configuration values and drug libraries.

Finally, the central management units of some related art systems are permanently attached to at least one infusion pumping unit. This is disadvantageous as many clinical situations only require simple patient monitoring, and the added expense of an attached infusion unit is unnecessary.

OBJECTIVES AND SUMMARY OF THE INVENTION

In view of the above disadvantages of the related art, it is an object of the present invention to provide a modular patient care system that may be easily upgraded and adapted to meet future user needs.

It is a further object of the invention to provide interchangeable central interface units with different levels of functionality so as to increase system safety and cost effectiveness.

It is yet a further object of the invention to provide an interface between the patient care system and external devices so as to facilitate the uploading and downloading of a wide range of information.

In accordance with the present invention, there is provided a modular, programmable patient care system comprised of an interface unit removeably attached to a plurality of patient functional units. The interface unit provides an interface between the user and the system, and may be either an advanced interface unit with a high level of interface functionality or a basic interface unit with a lower level of interface functionality. These units may be interchanged so as to provide increased flexibility, safety, and cost-effectiveness to the user. Each interface unit contains interface ports for the uploading and downloading of information such as drug libraries, drug infusion profiles, system configuration values, and event history.

The functional units of the patient care system provide patient monitoring and/or therapies. The functional units are internally programmed and controlled so as to provide greater system modularity, and require only the power, interfacing functionality, and overall system management from the central interface unit.

BRIEF DESCRIPTION OF THE DRAWINGS

These and other methods, structures, features, aspects, and advantages of the present invention will become more readily apparent from the following detailed description, which should be read in conjunction with the accompanying drawings, in which:

FIGS. 1A–1B show an advanced interface unit according to the invention, wherein FIG. 1A is a front view of the advanced interface unit removeably connected to a functional unit and FIG. 1B is a rear view of only the advanced interface unit;

FIG. 3 discloses a block diagram of an advanced interface unit;

FIGS. 4A–4B show a basic interface unit according to the present invention, wherein FIG. 4A is a front view and FIG. 4B is a rear view;

FIGS. 7 through 10 depict screen displays of an interface unit during the setup of a primary infusion;

FIGS. 11 through 12 depict screen displays of an interface unit during the setup of a secondary infusion;

FIGS. 13 through 14 depict screen displays of an interface unit during the setup and operation of a multidose infusion;

FIGS. 15 through 19 depict screen displays of an interface unit during the setup and operation of a multichannel coordinated infusion; and FIGS. 20 through 26 depict screen displays of an interface unit during drug infusion rate calculations.

DETAILED DESCRIPTION OF THE INVENTION

Figure 1A:
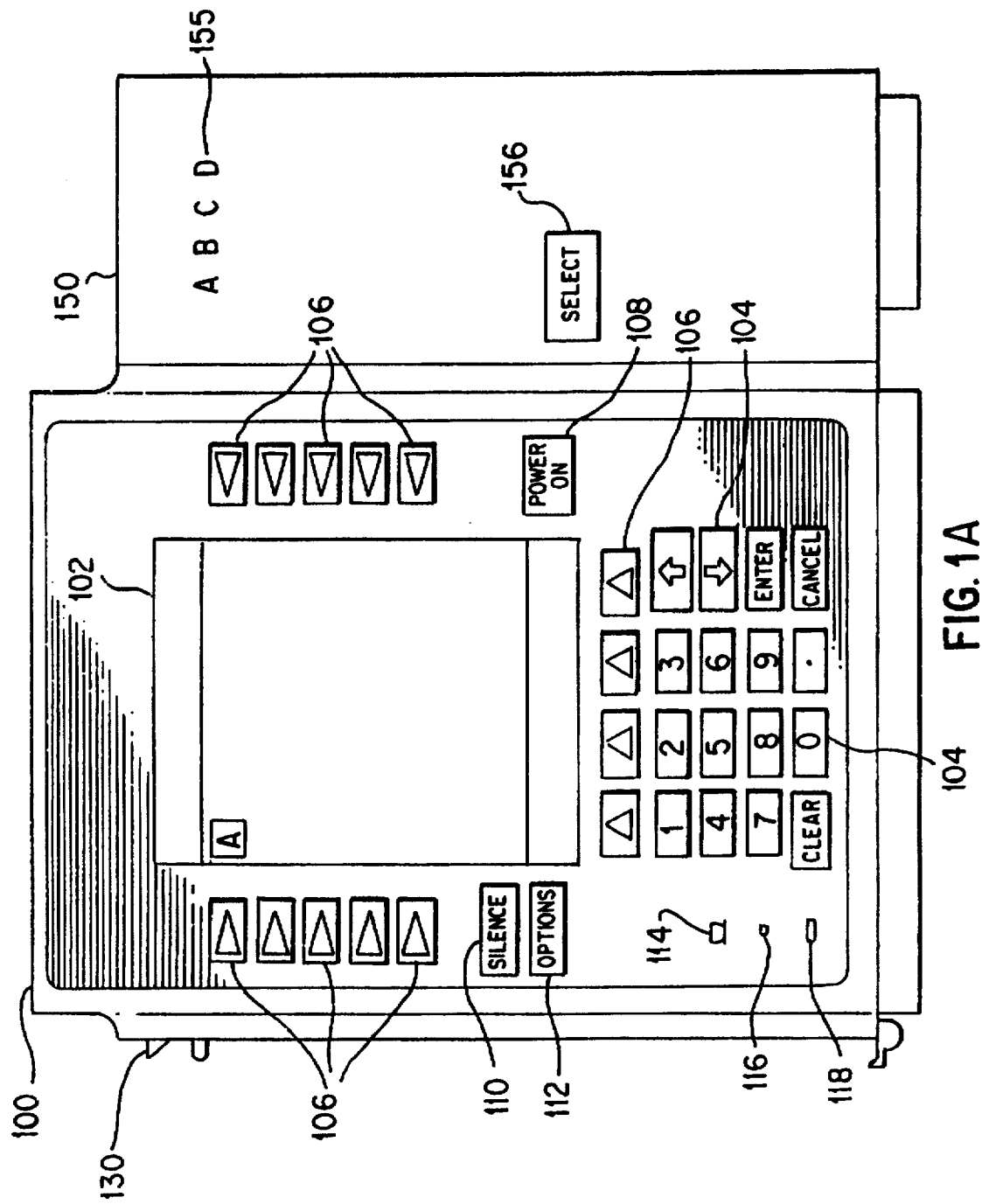

The following embodiments of the present invention will be described in the context of a modular patient care system.

although those skilled in the art will recognize that the disclosed methods and structures are readily adaptable for broader application. Note that whenever the same reference numeral is repeated with respect to different figures, it refers to the corresponding structure in each such figure.

Figure 1B:
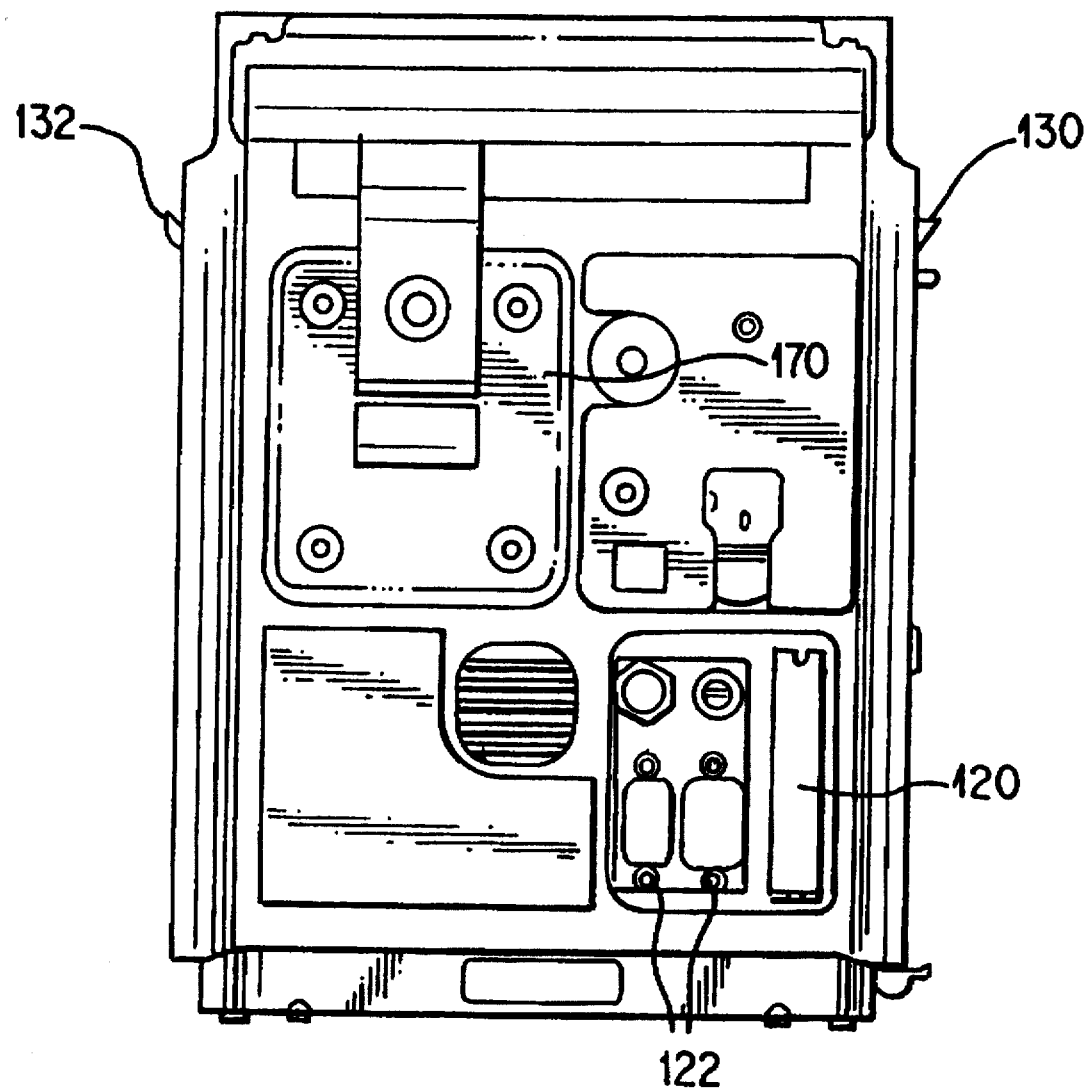

FIGS. 1A–1B disclose a modular, programmable patient care system. According to a preferred embodiment of the invention, this system comprises an advanced interface unit 100 and at least one functional unit 150.

Advanced interface unit 100 generally performs four functions in the patient care system: it provides a physical attachment of the system to structures such as IV poles and bed rails, it provides power to the system, it provides an interface between the system and external devices, and, except for certain specific information, it provides a majority of the user interface of the system. Advanced interface unit 100 contains an information display 102, which may be any type of display such as a liquid crystal display. Display 102 may be used during setup and operating procedures to facilitate data entry and editing. Display 102 may also be used to display various operating parameters such as volume to be infused (VTBI) for individual functional units 150 which are pumps and current time of day, as well as other prompts, advisories, and alarm conditions. Advanced interface unit 100 contains a plurality of hardkeys 104 and softkeys 106 for entering data and commands. The numerical hardkeys 104 are used for entering numerical data, while the remainder of the hardkeys 104, as well as the softkeys 106, are used for entering operational commands.

Softkeys 106 may be arranged along the edges of display 102 so as to interact with the display to define the function of a particular softkey 106 at any given time. Therefore, a particular softkey 106 when pressed will allow for the selection of an option, or an infusion or monitoring parameter, which is displayed on display 102 adjacent to the softkey. As noted, some hardkeys 104 are also used for entering specific operational commands. For example, hardkey 108 when pressed, causes the system to change from standby to operating mode. Alternatively, if hardkey 108 is pressed during a hardware malfunction, it can be used to silence audio alarms and turn off electrical power to advanced interface unit 100. SILENCE hardkey 110 may be used to temporarily disable the audio functionality of advanced interface unit 100, while OPTIONS hardkey 112 allows user access to available system or functional unit options as described in more detail in conjunction with FIGS. 7 through 26 below.

Advanced interface unit 100 also contains three indicators 114, 116, and 118. Indicator 114 may be used to indicate that the system is communicating with a compatible external computer system. Indicator 116 may be used to indicate that advanced interface unit 100 is connected to and operating with an external power source, and indicator 118 may be used to indicate that advanced interface unit 100 is operating with the use of an internal power source. Advanced interface unit 100 may also include a tamper-resistant control function (not shown in FIG. 1) which, when enabled, will lock out a predetermined set of controls.

Advanced interface unit 100 preferably also contains at least one external communication interface. A communication interface 120 is located at the rear of advanced interface unit 100. Communication interface 120 is preferably an industry standard personal computer memory card international association (PCMCIA) slot for receiving PCMCIA cards, although one skilled in the art could select from a variety of commercially available communication means.

Also located at the rear of advanced interface unit 100 is at least one interface port 122. Interface ports 122 are preferably industry standard RS-232 ports, although again, one skilled in the art could select from a variety of commercially available communication means. It is to be understood that although a preferred embodiment of the invention is described as containing an interface 120 and at least one port 122, any number or combination of communication interfaces and ports could be included in advanced interface unit 100.

Interface 120 and ports 122 illustratively may be used to download drug libraries, drug delivery profiles, and other system configuration values, or may be used to upload event history data from advanced interface unit 100. Interface 120 and ports 122 may also act as an interface to patient monitoring networks and nurse call systems, or as an interface to external equipment such as barcode readers to provide a means of inputting drug and/or patient information from medication or patient records. Performing these functions with ports 122 and interface 120 will advantageously provide greater functionality and adaptability, cost savings, and a reduction in input errors. Ports 122 and interface 120 may also be supplemented with a Patient Controlled Analgesia (PCA) port (not shown in FIG. 1). The PCA port provides a connection to a remote hand-held "dose request" button which can be used by a patient to request a medication dose during PCA applications.

Located on both sides of advanced interface unit 100 are unit connectors 130 and 132 which are used to attach the functional units 150 which directly contact advanced interface unit 100. These connectors 130 and 132 provide physical support for the attached functional units 150 and provide power and internal communication connections between the advanced interface unit and the functional units. As will be discussed below, functional units 150 also contain these unit connectors on either side so that functional units may be connected to the patient care system in a side-by-side manner. A suitable unit connector is described in U.S. Pat. No. 5,601,445, entitled ELECTRICAL AND STRUCTURAL INTERCONNECTOR and filed concurrently herewith, by the assignee of the present application. This copending patent is incorporated herein in its entirety by reference.

Finally, advanced interface unit 100 includes a clamp 170 on its rear surface for use in attaching advanced interface unit 100 to a structure such as an IV stand or a hospital bed. The clamp may be any clamp suitable for attaching bedside patient monitoring or infusion apparatus to these structures.

Also shown in FIG. 1A is a functional unit 150. It is to be understood that although only a single functional unit 150 is shown in FIG. 1A, any number of functional units 150 may be connected using the above described unit connectors in any order to either side of advanced interface unit 100. The type and number of functional units attached to advanced interface unit 100 is limited only by the physical and electric ability of the wiring and of the interface unit to handle the desired types and numbers of functional units. Functional unit 150 may be selected from a wide variety of functional units including those for patient therapies and patient monitoring. More specifically, functional unit 150 may be a standard infusion pumping unit, patient controlled analgesia (PCA) pump, syringe pump, pulse oximeter, invasive or non-invasive blood pressure monitor, electrocardiograph, bar code reader, printer, temperature monitor, RF telemetry link, fluid warmer/IV pump, or high rate IV pump (2000+ ml/hr). It is to be understood that this list is for illustrative purposes only and that one skilled in the art could adapt functional unit 150 for other uses.

Each functional unit 150 includes a channel position indicator 155 which identifies the position of the functional unit within a patient care system. As shown by position indicator 155 in FIG. 1A, a system may illustratively contain four channels, A, B, C, and D. If the system contains four functional units, the functional units will each be in one of the four channel positions A, B, C, and D, and the channel position indicator 155 on each individual functional unit will visually indicate the corresponding channel position. Preferably the channel positions are designated A–D, beginning with the first unit on the left. The positions of each functional unit may be interchanged, but the channel locations A–D stay in the same positions relative to advanced interface unit 100. Thus, for example, when four functional units are attached as in FIG. 2, regardless of which unit is placed immediately to the left of advanced interface unit 100, that unit will always indicate channel position B. As explained in detail below, the functional unit contains certain function specific information which tells advanced interface unit 100 what type of functional unit is at each channel position. Each functional unit 150 also has SELECT key 156, which permits selection of the unit.

Figure 2:
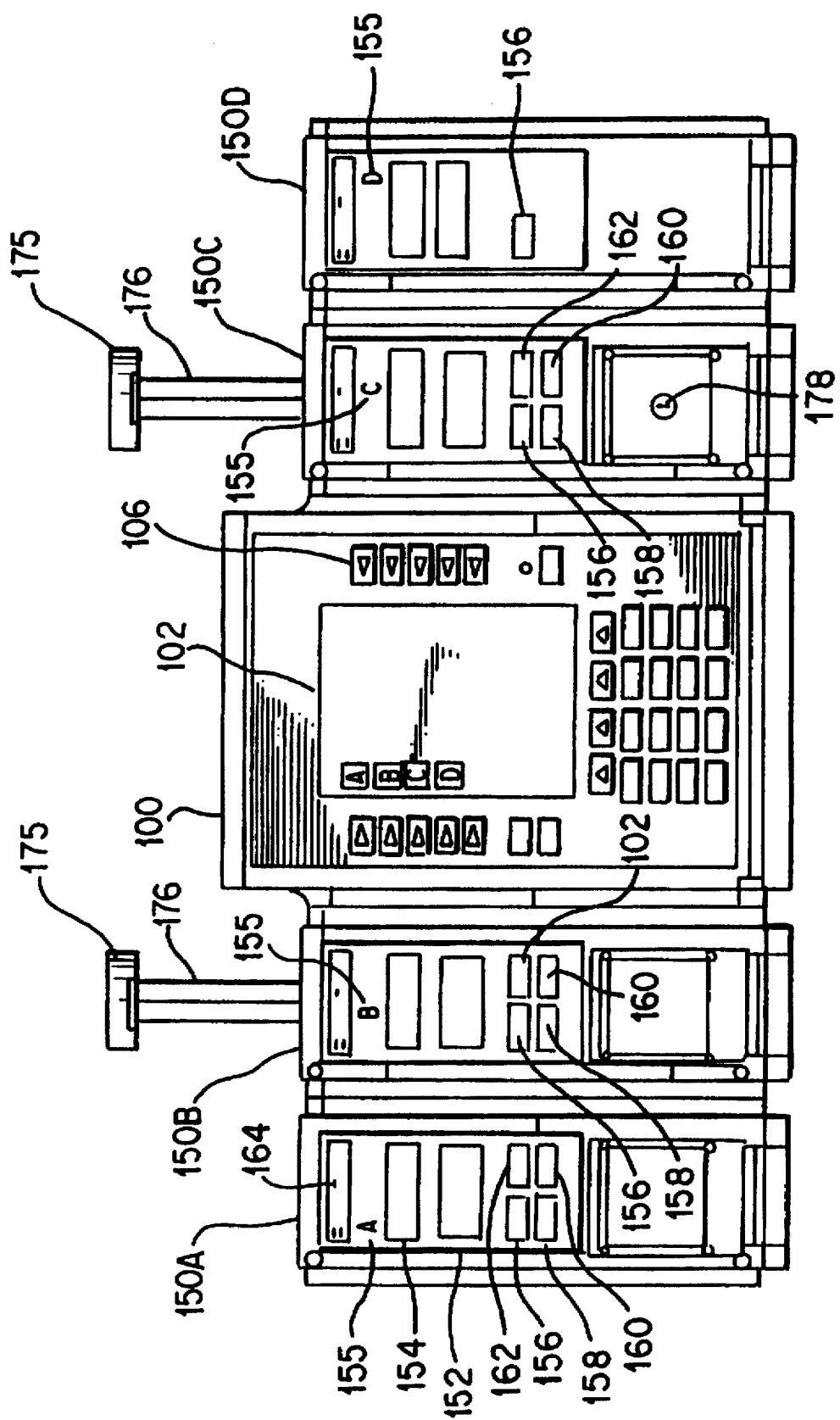
FIG. 2 shows a front view of an advanced interface unit removeably connected to four functional units.

FIG. 2 illustrates an exemplary system according to the present invention including four different functional units. Infusion pump unit 150A is at position A. Syringe pump 150B is at position B. PCA unit 150C is at position C, and pulse oximeter 150D is at position D. The respective position of each functional unit is indicated on the functional unit at indicator 155. Because four functional units are in use, display 102 on interface unit 100 indicates A through D. In one embodiment, it would be possible to select a functional unit to perform a particular function or procedure through advanced interface unit 100 by depressing the appropriate softkey 106 adjacent to the desired, indicated channel and functional unit. However, in order to provide increased safety, it is preferable that the system be designed such that selection of a particular functional unit requires that SELECT key 156 (see FIG. 1) located on the functional unit be depressed in order to select that functional unit. This requirement will help insure that the proper functional unit is selected, in particular when infusion pump units are used for multiple drug infusions. When the desired functional unit is selected, display 102 of the interface unit is configured so as to act as the user interface for the selected functional unit. More specifically, display 102 is configured in accordance with a function specific domain to provide function specific displays and softkeys as explained in greater detail below.

Infusion pump unit 150A shown in FIG. 2 is a pumping unit for basic fluid infusion. Infusion pump unit 150A includes a system to control the various functions performed by such a pump, which include the control of fluid delivery to the patient and the monitoring of the fluid path for occlusion or air-in-line. Infusion pump unit 150A contains two displays. Rate display 154 may be used to display the actual infusion rate at which the pump is operating. Channel message display 152 may be used to display informational, advisory, alarm, or malfunction messages.

The infusion pump control may also contain hardkeys for data and command entry. Hardkey 156, as mentioned, allows the user to select a channel for infusion parameter entry. Hardkey 158 allows the user to pause an infusion while the infusion is occurring. Hardkey 160 allows the user to resume operation of a previously paused infusion, and hardkey 162, when pressed, stops the infusion occurring on the channel, deselects the channel, and if the functional unit on the channel has been the only functional unit operating, powers off the system.

Infusion pump unit 150A also contains a plurality of indicators 164, which illustratively illuminate when the functional unit is in alarm or infusion complete condition, when the functional unit is programmed for a future start time or has been paused, or when the functional unit is performing an infusion. Other appropriate indicators may be included in other functional units.

Also shown in FIG. 2 is syringe pump 150B, PCA unit 150C, and pulse oximeter 150D. As shown, syringe pump 150B and PCA unit 150C each contain a set of hardkeys 156, 158, 160, and 162 like those found on infusion pump unit 150A. Syringe pump 150B and PCA unit 150C also contain a syringe 176 along with a syringe pusher 175 for manually infusing fluids. PCA unit 150C includes a door lock 178 for providing security for enclosed narcotics or other matter to be infused. In addition, pump 150B, PCA unit 150C and pulse oximeter 150D each include one or more displays and a plurality of indicators which may be used to display appropriate information.

As mentioned, located on the sides of infusion pump unit 150A, as well as all other functional units, are unit connectors (not shown in FIGS. 1A–1B and 2) which are identical to unit connectors 130 and 132 of advanced interface unit 100 disclosed in FIGS. 1A–1B. As mentioned previously, the unit connectors of the functional units 150 are designed to mate with either the connectors on an interface unit or with the connectors from another functional unit. In this manner, a plurality of functional units 150 may be connected side by side in any order on both sides of advanced interface unit 100. It is to be understood that these unit connectors between advanced interface unit 100 and a functional unit 150 or between two functional units may be made permanent or semi-permanent by some mechanical means such as a screw or a nut and bolt combination. This has the advantage of preventing unintentional or unauthorized detachment of functional units from the system, or to conform to medical institution policy.

FIG. 3 is a schematic diagram for advanced interface unit 100. As shown in FIG. 3, advanced interface unit 100 contains a power input 268 for receiving power from an external power source and forwarding that power to power supply 258. Advanced interface unit also contains an internal power source 262 which may be used to maintain power to the system functions, including memory, when advanced interface unit 100 is disconnected from an external power source. Power supply 258 converts power from either external power input 268 or internal power source 262 to voltages which are appropriate for operating all parts of the system. Power manager 254 controls the switchover between the two power sources, controls the charging of internal power source 262, monitors the remaining capacity of internal power source 262, monitors system power consumption under battery operation, and uses system power consumption and remaining battery capacity to estimate remaining system runtime on internal power source 262. Power supply 258 also supplies power to the rest of the system through power ports 278 and 279 as well as to audio alarm 260, thereby enabling the audio functionality of the system.

Microprocessor 264 and memory 250 receive and process data and commands from the user, as well as communicate with and control functional units 150 and other devices external to the system. It is to be understood that memory 250, as well as other memories in the patient care system, may be any type of memory or any combination of memories that can be erased and reprogrammed without having to physically remove the memory from the system. Examples of such memories include, but are not limited to, batterybacked random access memory (RAM) and "flash" electronically erasable programmable read only memory (FLASH EEPROM). Battery backup 256 provides power to memory 250 to maintain the information stored in the memory in the event of loss of power from both the power input 268 and the internal power source 262. Advanced interface unit 100 also contains a keyboard 266 (comprised of hardkeys 104 and softkeys 106) and a display 102 as discussed in conjunction with FIG. 1.

Power ports 278 and 279, fed by power supply 258 provide power to functional units 150 through connectors 130 and 132, respectively (shown in FIGS. 1A-B). Connectors 130 and 132 also contain internal communication ports 280 and 281, respectively, which provide a data and command interface with attached functional units 150. Ports 280 and 281 are controlled by internal communications controller 272, which in turn is controlled by microprocessor 264. Finally, external communications controller 274 controls the command and data flow through interface ports 122, while microprocessor 264 directly controls communication interface 120.

Figure 4A:
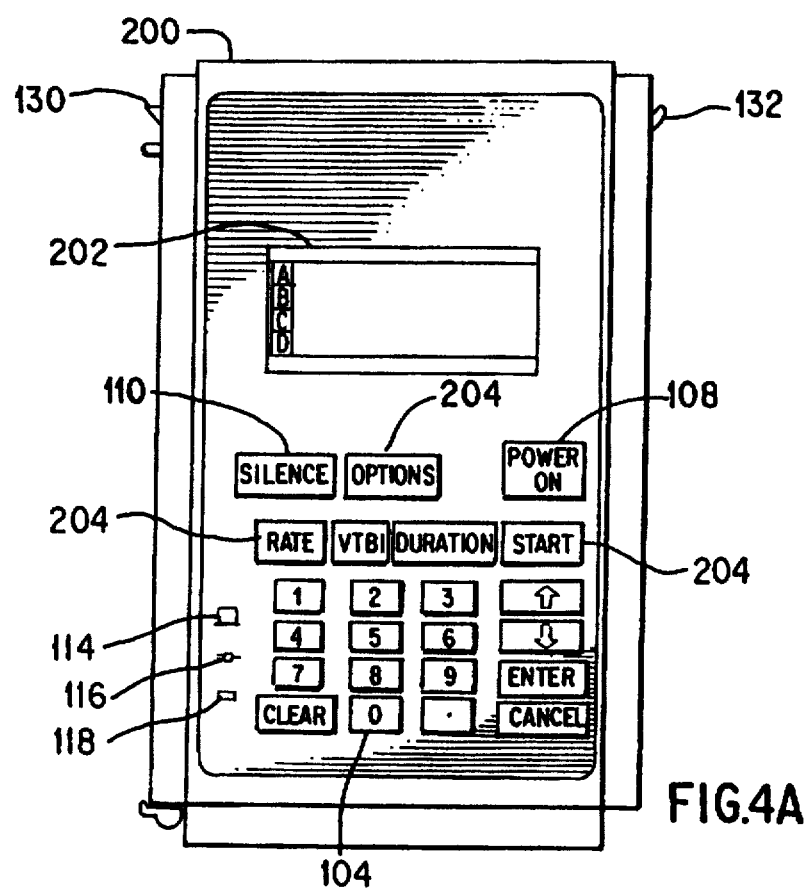
Figure 4B:
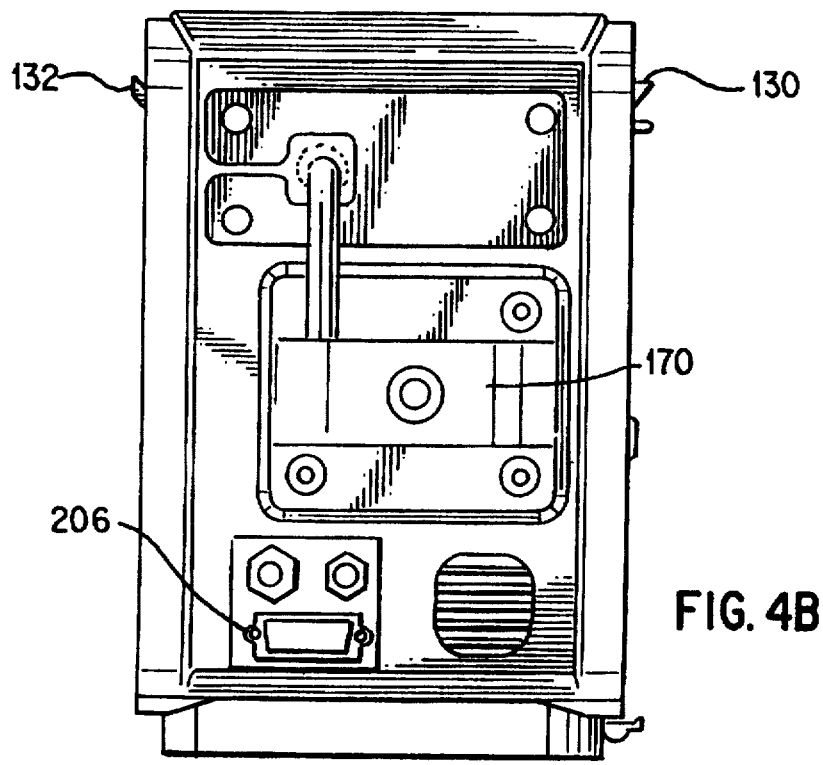

FIGS. 4A-4B illustrate basic interface unit 200. Like advanced interface unit 100, basic interface unit 200 provides a physical attachment of the patient care system to structures such as IV poles and bed rails (through clamp 170), provides an interface between the patient care system and external devices, provides power to the system, and provides a user interface to the system. Thus, according to a preferred embodiment of the invention, basic interface unit 200 performs many of the same functions as, and may be used interchangeably with, advanced interface unit 100. The interchangeability of basic interface unit 200 with advanced interface units 100 is advantageous because in some non-critical clinical situations it is efficient to operate the patient care system with a user less skilled than a professional such as an anesthesiologist. In these situations, use of the functionally complex advanced interface unit 100 might introduce a risk of error and confusion. Therefore, in these non-critical situations, use of basic interface unit 200 may be beneficial. Moreover, in these situations, the full functionality of advanced interface unit 100 is often not required. Thus, basic interface unit 200 provides a safe, cost-effective interface for the patient care system.

Basic interface unit 200 can also provide a cost effective alternative for patients whose level of criticality varies during a hospital stay. It is contemplated that advanced interface units 100 may be assigned to areas in the hospital, such as intensive care units, where its high level of functionality and versatility may be fully utilized. However, when a patient's condition improves, the advanced functions of an advanced interface unit 100 may not be required. Thus, areas such as the general care ward of a hospital may be equipped with basic interface units 200 to care for patients whose condition is no longer critical. In this manner, functional units 150 can be quickly and easily interchanged between interface units in different areas of the hospital. Moreover, the memory of the functional units 150 can recall the last operation performed by the unit so that the function may be quickly resumed in response to a prompt from the newly attached interface unit. As can be seen from FIG. 4, basic interface unit 200 also contains many of the same features found in advanced interface unit 100. For example, hardkeys 104 are used for entering data and commands, while indicators 114, 116, and 118 may be used to indicate that the system is communicating with a compatible external computer system, or that an external or internal power source is being utilized. Hardkey 108 may be used to power on the system, while hardkey 110 may be used to disable system audio functionality. The OPTIONS hardkey 204 of basic interface unit 200 allows access to the available system or channel options in the same fashion as OPTIONS hardkey 112 of advanced interface unit 100. Finally, unit connectors 130 and 132 provide physical support to the attached functional units 150 (not shown) and provide power and communication connections between the basic interface unit 200 and the functional units.

Like advanced interface unit 100, basic interface unit 200 may also contain external communication ports or interfaces. However, in a preferred embodiment of the invention, basic interface unit 100 contains only a single interface port 206, preferably an RS-232 port, which may be used to input data into the system or output data from the system, as well as control system operations in certain applications. Interface port 206 may also be used to communicate with external equipment such as barcode readers.

In accordance with a preferred embodiment of the invention, basic interface unit 200 also contains information display 202 which may be used during operation to display various operating parameters, such as VTBI, current time of day, as well as other prompts, advisories, and alarm conditions. Display 202 may also be used during setup and other operational procedures to facilitate data and command entry. However, display 202, unlike display 102 of advanced interface unit 100, may not be used in conjunction with a set of softkeys to enter commands. Basic interface unit 200 also contains a set of hardkeys 204, labeled VTBI, RATE, DURATION, and START, that are not found in advanced interface unit 100. These keys may be used to enter or change the parameters or start the infusion process on a selected channel. Therefore, in a preferred embodiment, basic interface unit 200 is intended principally for controlling infusions and does not have the higher level of functionality of advanced interface unit 100 (which may complicate its operation and increase its cost) that is necessary for controlling other patient therapies and patient monitoring. In fact, in an alternative embodiment of the invention, basic interface unit 200 may be configured so as to provide only power to the attached functional units 150. Thus, based on the teachings set forth herein, a person of ordinary skill in the art may select and design a desired level of functionality for the basic interface unit depending on system requirements.

Figure 5:
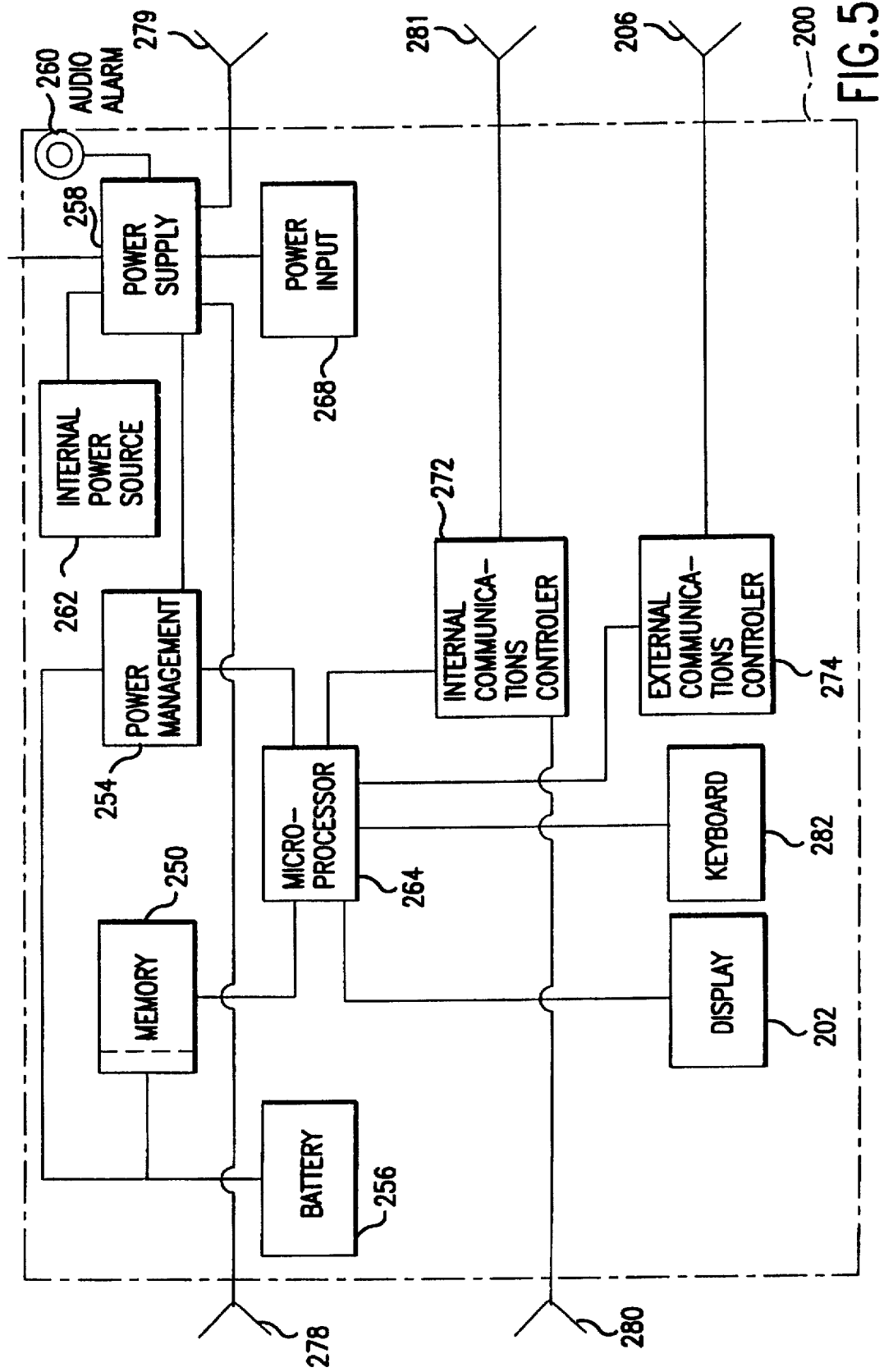
FIG. 5 discloses a block diagram of a basic interface unit.

FIG. 5 discloses a schematic of basic interface unit 200. As seen from FIG. 5, the basic interface unit is internally similar to advanced interface unit 100. However, as explained, in a preferred embodiment of the invention, basic interface unit 200 does not contain communication interface 120 (which is preferably a PCMCIA slot in advanced interface unit 100). Moreover, as previously disclosed, display 202 and keyboard 282 are different than the corresponding structures in advanced interface unit 100.

Figure 6:
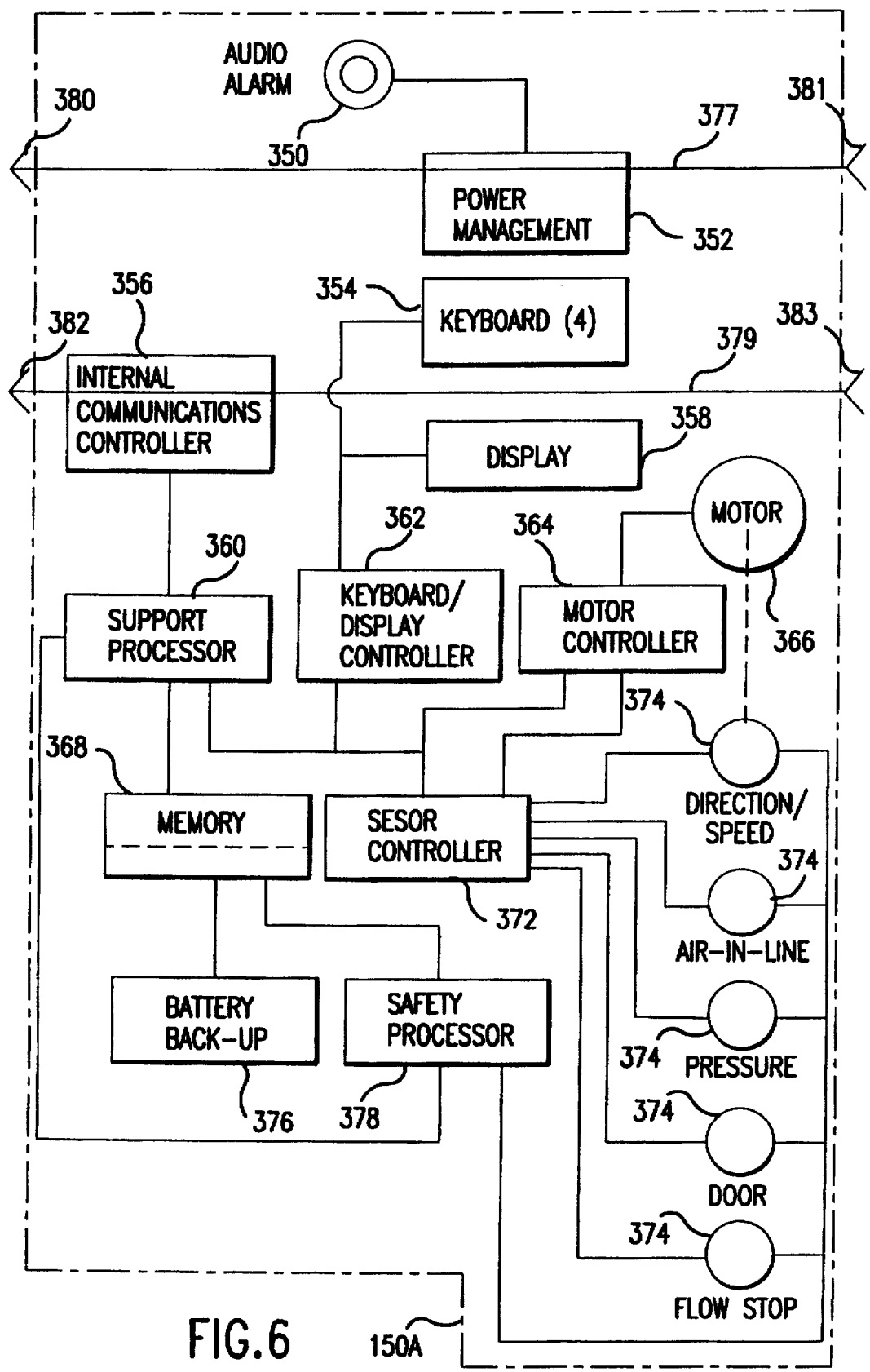
FIG. 6 discloses a block diagram of a functional unit according to the invention.

FIG. 6 is a block diagram which illustrates the various aspects of the control system for infusion pump unit 150A. Display 358 comprises rate display 154, channel display 152, and the various visual indicators 164 discussed in conjunction with FIG. 2. Keyboard 354 is made up of the various hardkeys as also previously discussed, and is controlled, along with display 358, by keyboard/display controller 362. Support processor 360 and associated memory 368 allow infusion pump unit 150A to receive and process data and commands from the user, as well as communicate with the attached interface unit. Specifically, support processor 360 and memory 368 allow the infusion pump unit to perform the calculations required for a designated infusion using infusion data entered by the user. Memory 368 has a battery backup 376 so as to maintain the information stored in memory when the functional unit is not receiving power from an external source. Battery backup 376 may also be used to power audio alarm 350, which may emit a signal illustratively when an infusion is complete or there is a failure of the main power source. Power manager 352 obtains power from power ports 380 or 381, which are included in the unit connectors (discussed in conjunction with FIGS. 1–2) which connect the functional units to the interface unit or other functional units, through power line 377 and distributes the power to the components of infusion pump unit 150A. Like the interface units 100 and 200, infusion pump unit 150A also contains an internal communications controller 356, which may send or accept data or commands from the interface unit through communication line 379 and communication ports 382 and 383, said ports also contained in the unit connectors. As mentioned, these power and communication ports connected by the power and communication lines are advantageous as they allow functional units to be connected side-by-side, yet still communicate with the interface unit while not directly attached to the interface unit.

Infusion pump unit 150A also contains typical components of commercially available pumps, such as motor controller 364 for controlling pump motor 366 and sensor controller 372 to obtain indications from sensors 374 which illustratively may be used to detect pump mechanism speed and fluid pressure, air-in-line, and flow stoppage. Motor controller 364 and pump motor 366 may be comprised of any suitable peristaltic pump motor/motor controller combination. Pump motor 366 acts to force fluid from a fluid reservoir through an infusion set to a vascular access device by peristaltic motion such as disclosed in U.S. Pat. No. 5,165,873 to Meijer. It is to be further understood that one skilled in the art could choose from a variety of commercially available fluid reservoirs, sets, vascular access devices and other infusion materials to use in conjunction with infusion pump unit 150A.

Again in a known manner, sensor controller 372 receives signals from sensors 374 which illustratively sense pump motor direction and speed, the presence of air in the fluid path, fluid path pressure, open or closed state of the pump door, and open or closed state of a flow stop device, and forwards this information to support processor 360. If support processor 360 determines that an undesired event is occurring, the support processor is capable of taking further action such as placing pump unit 150A in an advisory or alarm state, stopping the infusion, shutting down the pump unit, and/or forwarding information to the attached interface unit for full system shutdown.

Safety processor 378 monitors these same signals from sensors 374. Safety processor also receives pump operating parameters from support processor 360 such as current infusion rate, VTBI, and fluid path pressure alarm limits. Safety processor 378 independently calculates values such as the appropriate motor speed from these parameters, and using these values, monitors sensors 374 for proper pump motor direction and speed, the presence of air in the fluid path, fluid path pressure, open or closed state of the pump door, and open or closed state of the flow stop device. If safety processor 378 determines that an undesired event is occurring, this information is forwarded to support processor 360 for further action, or the safety processor may independently shut down the functional unit. Configuring the system in this manner has the advantage of allowing the functional unit to detect and respond to single fault conditions such as failure of sensor controller 372 or support processor 360.

It is to be understood that infusion pump unit 150A (nor any other functional unit 150 as presently contemplated) does not have a local source of power (with the exception of the memory retention and the audio alarm features described above), and therefore will not continue to operate in the event of failure of the main power source, such as when the functional unit is detached from the interface unit. This ensures that the functional unit is not operated without the safety and control features provided by the interface units. Also, the simplified commands available directly at the pump functional unit are not intended to replace the interface capabilities of advanced interface unit 100 or basic interface unit 200. However, when provided with power and the necessary input values (such as VTBI and infusion duration) from the interface unit, the infusion pump unit as a functional unit is capable of controlling all aspects of an infusion.

As a further advantage of the present invention, there is provided multiple levels of redundancy in the patient care system. Specifically, in addition to the safety architecture of the functional units, the interface unit contains its own safety architecture which frequently checks the functional units to verify that they are working properly. If the interface unit is satisfied that the functional units are functioning properly, then it allows continued operation of these functional units. However, if the interface unit determines that a functional unit is malfunctioning, it may shut down that particular functional unit or, alternatively, the entire system. Illustratively, if the functional unit in operation is an infusion pump unit, the infusion pump safety system would make frequent calculations using the desired infusion parameters to ensure the accuracy of the infusion. At the same time, the interface unit attached to the infusion pump unit could request information regarding the ongoing infusion from the pump, such as the volume infused, and make calculations based on this information and the infusion parameters to determine whether the pump is working properly.

In accordance with a preferred embodiment of the invention, the patient care system as described may be programmed so as to provide a wide variety of functions and features to meet various user needs through the use of the interfaces of advanced interface unit 100 and basic interface unit 200. As discussed in conjunction with FIG. 1, advanced interface unit 100 contains an interface 120 which is, in a preferred embodiment of the invention, a PCMCIA interface slot. Advanced interface unit 100 and basic interface unit 200 also contain ports 122 and 206, respectively, which in a preferred embodiment are industry standard RS-232 serial I/O ports. These interfaces and ports may be used to download drug libraries and drug delivery profiles to the system, download configuration values to the system, download new software or firmware to the system, and upload event history from the system. The interfaces and ports may also be used to control system operation in certain situations, receive input from external devices such as barcode readers, and send current operating data to external devices such as monitoring systems. It is to be understood that although these exemplary uses of the interfaces and ports may be described below using one type of interface or port as an example, one skilled in the art will understand that many commercially available interfaces could be used.

As mentioned, an interface or port may advantageously be used to download drug libraries to the patient care system. These drug libraries, which illustratively contain such information as the drug names, proper concentrations, dosage units, and dose limits of various drugs, can be used to perform drug calculation based infusions. An external device such as a personal computer can be used to create drug libraries, which can be customized for each user of the patient care system, and store these libraries on a PCMCIA memory card. A PCMCIA interface can then be used to download the drug libraries to the interface unit, where it can then be stored in permanent or semi-permanent memory for later use.

An interface or port can also be used to download complex drug delivery profiles, or infusion protocols, to the patient care system. Various drug delivery profiles are known within the medical field. These profiles include Versataper® multiple rate volume infusions, Autotaper® automated ramp up taper down infusions, multi-channel coordinated infusions, and multi-dose infusions. As is the case in the downloading of drug libraries, complex drug delivery profiles can be created and then stored on PCMCIA memory cards. A PCMCIA interface can then be used to download the drug delivery profiles to the system, where they can then be stored in permanent or semi-permanent memory within the interface unit.

The interfaces or ports of the patient care system also allow the user to download new system configuration information and values. Examples of such values are port setup (baud rate, byte size, etc.), maximum allowed flow rate, user interface reconfiguration information, and language selection. It is to be understood that the interfaces or ports may be used to download system configuration values to the advanced interface unit 100, basic interface unit 200, or functional units 150. Specifically, in accordance with a preferred embodiment of the invention, to download configuration values to advanced interface unit 100, microprocessor 264 in advanced interface unit 100 can obtain the new values from a PCMCIA card containing the new values, and store the new values in memory 250. To download configuration values to functional unit 150, microprocessor 264 in advanced interface unit 100 can obtain the new values from the PCMCIA card and send the values to functional unit processor 360 which will store the new values in functional unit memory 368. To download configuration values to basic interface unit 200, microprocessor 264 of advanced interface unit 100 can obtain the values from the PCMCIA card and send the values to basic interface unit microprocessor 264 preferably across an RS-232 port connecting the two interface units. Microprocessor 264 can then store the values into basic interface unit memory 250.

An interface or port may also be used to upgrade the patient care system with new software or firmware for new applications or to enhance performance. A specific example of this is when a new functional unit is added to the system which performs a function not previously available on the system. In this situation, a software domain corresponding to the new function must be downloaded to any advanced interface unit 100 which the new functional unit is to be attached to. In an alternative embodiment, software domains may also be downloaded to basic interface unit 200. The software domain corresponding to the new function allows the interface unit(s) to understand and recognize the function of the functional unit and configure its user interface in a manner which permits a user to setup and perform the function. Therefore, because the interface unit provides the user interface for each function available in the system, the interface unit must initially contain or later be provided with, a software domain for each function to be performed.

To download a new domain to advanced interface unit 100, microprocessor 264 of the advanced interface unit obtains the new domain to be added through an interface, preferably a PCMCIA interface, and then stores the new domain in memory 250. Likewise, when downloading a new domain to basic interface unit 200, the basic interface unit to be upgraded is first connected to advanced interface unit 100 using preferably an RS-232 port on each of the interface units. The advanced interface unit then obtains the new domain preferably from a PCMCIA card, and transfers the domain to the basic interface unit through the RS-232 ports. The basic interface unit may then store the new software in its memory 250.

It is to be understood that in an alternative exemplary embodiment of the present invention, the domain corresponding to the new function may be stored in the functional unit performing the function, rather than in the interface unit. Storing the software domain in this manner will allow the functional units to use the domain to configure the user interface of the interface unit so that the user can setup and perform the function.

It is to be further understood that although the software domain of a functional unit may be stored in either the interface unit or the functional unit, functional unit identification information must always be stored in the memory of each functional unit. The identification information includes a means for uniquely identifying each functional unit, preferably a serial number, so that, for example, the event history of each functional unit can be followed and uploaded. The identification information also includes a means for identifying to the interface unit the function of the functional unit, such as a code to indicate that the functional unit is, for example, a pump. This information allows an interface unit storing a plurality of software domains to know which domain to access for the selected functional unit. Thus, the identification information stored in each functional unit not only uniquely identifies the functional unit to an attached interface unit, but identifies the functions of the functional unit as well. This identification information, as well as the software domain corresponding to a type of functional unit comprises information specific to each functional unit.

The functional units may also be upgraded over time. When upgrading the functionality of a functional unit 150, the functional unit to be upgraded is first attached to an interface unit. The interface unit obtains the new software through an interface, and then sends the software to support processor 360 in the functional unit across the internal communication lines in the patient care system. Support processor 360 then stores the new software or domain in memory 368.

An interface may also be used to upload event history to an external device. Each interface unit and functional unit within a patient care system has the capability of retaining information regarding its event history, including such information as infusion parameters, start time and end time of an infusion, incidents of alarms or advisories, and internal system errors. This event history illustratively may be used for updating patient records or troubleshooting. Although event history can be uploaded from each interface unit or functional unit, upload of functional unit event history will only be possible by using either advanced interface unit 100 or basic interface unit 200. Therefore, when uploading advanced interface unit 100 or basic interface unit 200 event history, the interface unit sends its event history directly to an external device. However, when uploading functional unit 150 event history, functional unit 150 must first be attached to an interface unit. Functional unit 150 then transfers its event history to the attached interface unit. The attached interface unit can then upload this information to an external device using its external interface.

In addition to the above features and functions that may be accomplished through the use of an interface or port, the interfaces or ports may also be used to control system operation, receive input from external devices such as barcode readers, and send current operating data to external devices such as monitoring systems. Although in a preferred embodiment of the invention, these functions may be accomplished through the use of ports 122 or 206, these functions may also be accomplished through the use of interface 120, and one skilled in the art will understand that many other types of commercially available interfaces and ports could be used to perform these functions.

In particular, a port may be used to control the operation of the patient care system in certain situations such as closed-loop drug delivery and manufacturing operational testing. To externally control the system, an external device such as a computer is connected to advanced interface unit 100 or basic interface unit 200 via the port. The interface unit may then be placed in "computer control" mode, which allows an external device to control certain system operations through the interface unit microprocessor.

A port may also be used to receive input from external devices such as barcode readers. This is advantageous in that it reduces manual input by the user and hence, reduces input errors. Illustrative examples of such input are drug dosing on prescription medications, patient information from patient records, and system control information. If such input is intended for use by a functional unit, the interface unit receiving the information can simply transfer information to the functional unit in the manner previously described.

The ports of the patient care system may be used to send current operating information to external systems for patient monitoring, patient diagnostics and other uses. Examples of these systems are centralized patient monitoring systems such as STATUS™, generalized hospital information systems for patient data and billing, and patient data collection systems for clinical studies. If current data from a functional unit 150 is required, the interface unit can request this information and forward it on to the external device or system.

As noted, the patient care system according to the present invention is comprised of an interface unit and a plurality of functional units that may be configured so as to provide a wide variety of functions to meet various user needs. These functions will now be described in conjunction with figures which show the state of the advanced interface unit display 102 on a step by step basis during system operation. It is to be understood that in a preferred embodiment of the invention, a predetermined subset of these functions may also be performed using basic interface unit 200.

FIGS. 2 and 7 through 10 illustrate the state of the advanced interface unit display 102 as the user interacts with the patient care system to perform a primary rate/VTBI infusion, one illustrative function of the system. FIG. 2 shows display 102 when advanced interface unit 100 is initially powered on. As previously described, each functional unit which is connected to the interface unit occupies a channel in the system, which may be labeled A, B, C, and D in a four unit system. The A, B, C, and D in display 102 advises the user that all functional units are communicating with the interface unit and may further be used to indicate the status of each functional unit occupying each respective channel in the system.

As previously discussed, each functional unit is designed to perform one or more specific functions. The functional units contain all the necessary hardware (e.g., the pumping mechanism for an infusion pump unit) for performing a designated function, as well as a processor and a self-contained and preprogrammed memory necessary to perform the calculations required for a designated function, as previously explained. In a preferred embodiment of the invention, all that is required of the interface unit is that it store the function domain and configure the user interface in accordance with the domain to permit the user to set up and run the designated function (although as noted, in an alternative embodiment, the user interface is configured by the functional unit). Thus, when a function is desired by a user, the interface unit provides the user interface for the setup and performance of the function, while the functional unit performs all the calculations required by the function. This is advantageous when combined with the fact that the user must actually press the SELECT key 156 on the actual functional unit to select that unit for an operation, as added safety and redundancy is provided.

By way of non-limiting example, the use of the system according to the present invention is explained in greater detail below by reference to infusion procedures using infusion pump unit 150A. To initiate a primary rate/VTBI infusion, the user must select an infusion pump unit and its corresponding channel to perform the infusion. To do so, the user presses the SELECT hardkey 156 (shown in FIG. 2) of infusion pump unit 150A. (Other types of functional units such as an electrocardiograph, syringe pump, PCA, and pulse oximeter, used with the present invention will have similar SELECT keys.) FIG. 7 shows display 102 after the user has selected the functional unit occupying channel A to perform the infusion. Once the channel A infusion pump unit has been selected, display 102 shows an infusion setup screen, which allows the user to input desired rate and VTBI values for the infusion.

FIG. 8 shows display 102 after the user has entered values for both rate (40 ml/hr) and VTBI (240 ml). The user enters the rate value in a preferred embodiment of the invention by pressing the softkey 106 adjacent to RATE and then using the numeric hardkeys 104 to enter the value. Entry of a VTBI value is performed in similar fashion.

Once these values have been entered, the infusion set corresponding to the programmed infusion pump unit 150A can be attached to the patient's vascular access device. The user can then press the softkey 106 adjacent to START to begin the infusion. Alternatively, the user can enter a future time at which the infusion is to begin. If the user chooses to utilize the delayed start feature, a real time clock in the interface unit will allow the system to begin the infusion at the desired future time.

Figure 10:
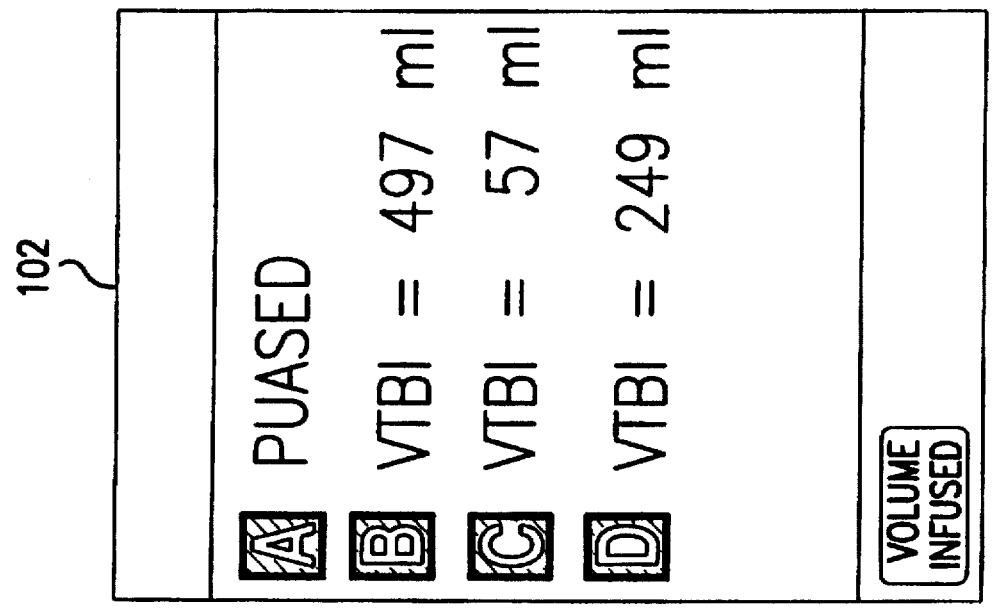
Figure 9:
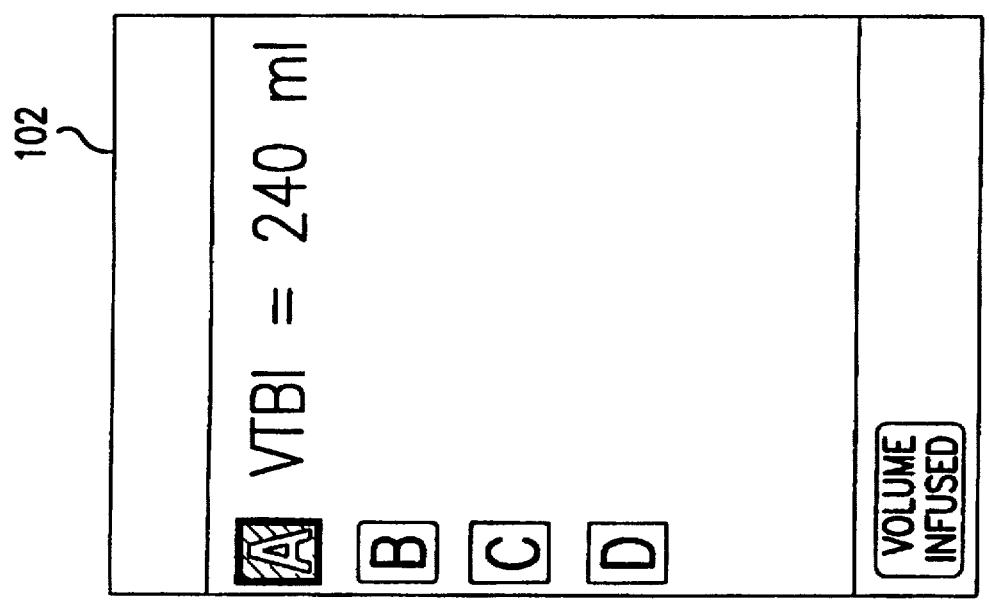

FIG. 9 illustrates the status of display 102 once the infusion has commenced. As can be seen from FIG. 9, display 102 discloses the status (VTBI=240 ml) of channel A during the infusion. Infusion rate displays on rate display 154 and infusing indicator 164 on pump functional unit 150A will also flash during the infusion. At any time during the infusion, the user may pause the infusion by pressing PAUSE hardkey 158 on the infusion pump unit which is infusing. FIG. 10 illustrates the status of display 102 while the functional unit A is paused (and the other three functional units, in this example all pump units, B, C, and D, are infusing). The user may then press RESTART hardkey 160 on the functional unit to reinstate the infusion. The rate or VTBI of an infusion may be changed at any time during the infusion by selecting the appropriate channel and then using the interface unit keypad to change the rate or VTBI values in the same manner that they were initially entered. The infusion may be stopped at any time by pressing the CHANNEL OFF hardkey 162 on the appropriate infusion pump unit 150A. At the completion of the primary rate/VTBI infusion, audio alarm 260 will sound and display 102 will visually indicate that the infusion is complete.

To perform an infusion, the user may alternatively choose to enter a VTBI and duration (infusion time) value rather than VTBI and rate values. From the entered VTBI and duration values, the infusion pump unit determines the corresponding rate, and the user may proceed as described above.

In accordance with the invention, the user can also program a secondary infusion with different rate and VTBI values. To do so, the user must first setup the primary infusion as described. The user may then press the softkey 106 adjacent to SECONDARY shown in FIG. 11 to enter rate and VTBI values for the secondary infusion. FIG. 12 shows display 102 after secondary rate and VTBI values have been entered for infusion pump unit 150A. Once these values have been entered, the user may press the START softkey 106 shown in FIG. 12 to begin the secondary infusion. Once the secondary infusion is complete, the system will return to and complete the primary infusion. However, the user has the option of stopping the secondary infusion at any time and returning the system to the primary infusion. The delayed start feature described in conjunction with the primary infusion may also be used to begin the secondary infusion at some time in the future.

The user has the further option of programming a multi-dose infusion. To set up a multidose infusion, the user may press the SELECT hardkey 156 on the desired pump functional unit, press the OPTIONS hardkey 112 on the interface unit, and then select the MULTIDOSE option. FIG. 13 illustrates display 102 once these steps have been taken. At this point, the user can enter values for rate, volume/dose, dose interval, number of doses, and start time. FIG. 14 shows display 102 after these values have been entered. The user can then press the START softkey shown in FIG. 14 to enable the multidose function. Once the current time equals the start time, the first dose infusion will begin.

The user also has the option of performing a multichannel coordinated infusion. To do so, the user must first prime and load the infusion sets for the desired pump functional units. The user can then press the OPTIONS hardkey 112 and select the MULTICHANNEL COORDINATED INFUSION option. FIG. 15 shows display 102 once the multichannel program has been selected. At this point, the user can enter rate and VTBI values for a maintenance infusion as previously described. The user also has the option of utilizing a flush between infusions. If a flush is required, the user can enter VTBI and duration values for the flush as shown in FIG. 16. FIG. 17 shows display 102 once all values have been entered. The user may then press softkey 106 adjacent to the NEXT shown in FIG. 17 to enter the parameters for the next infusion to be included in the multichannel infusion. At display 102 of FIG. 18, the next channel to be included may be selected using softkeys 106 of advanced interface unit 100. The user then enters the rate and VTBI values for this next channel, as well as the desired start time. The system now displays a summary screen, shown in FIG. 19, which gives a graphic presentation of the multiple programmed infusions. It is to be understood that the above process may be repeated to include as many infusion pump units as are attached to the system.

Another feature of the patient care system according to the invention is the ability to perform drug infusion rate calculations. In general, the drug calculation function of the system allows the user to either enter the desired drug dose and the infusion pump unit microprocessor calculates the correct flow rate to achieve the desired dose; enter the desired flow rate and the pump functional unit calculates the corresponding drug dose; or enter the desired bolus dose and duration and the pump functional unit calculates the bolus rate and the VTBI.

Figure 20:
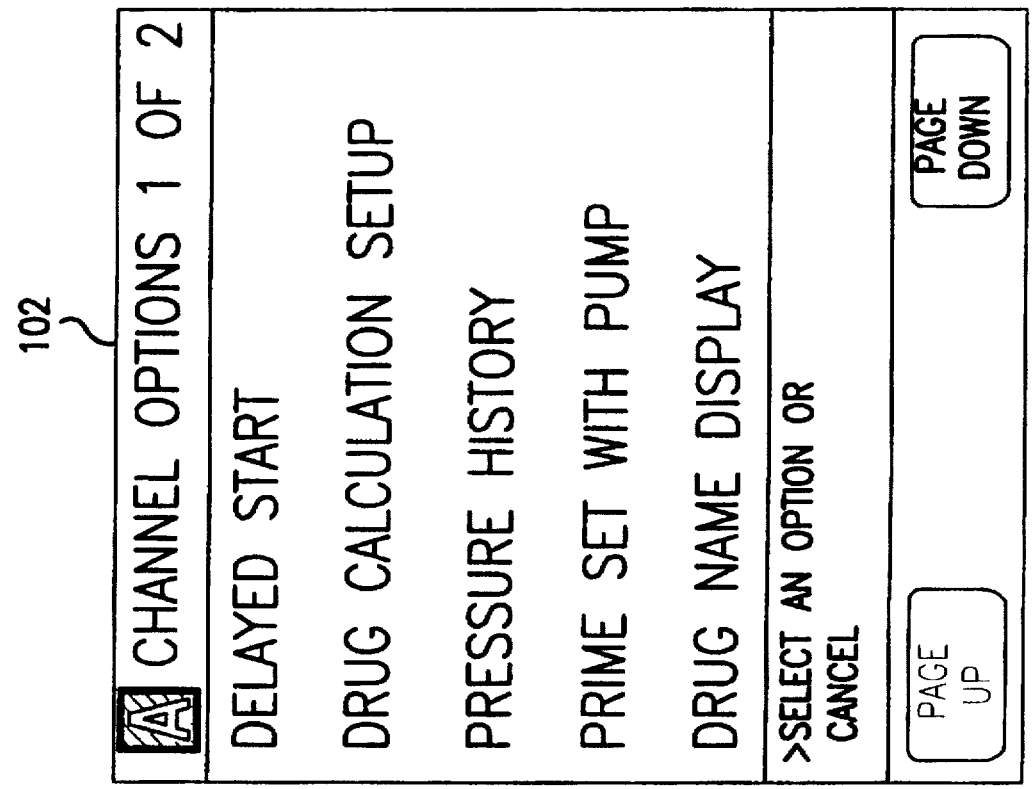
Figure 19:
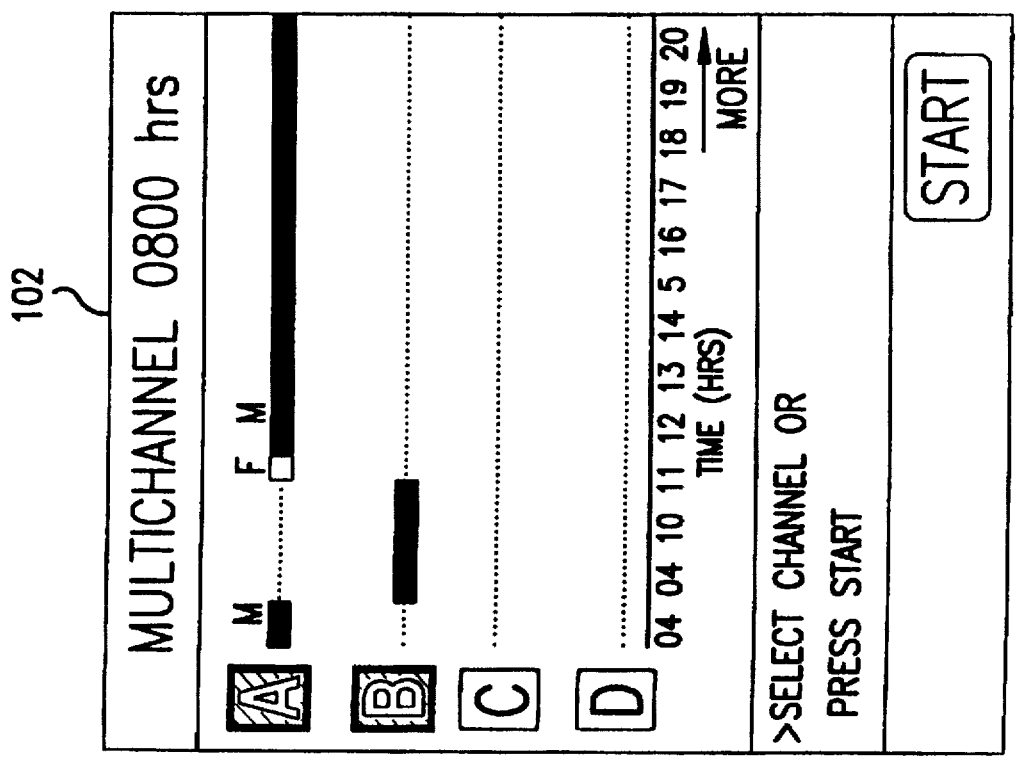

To enter the drug calculation mode, the user must press the SELECT hardkey 156 on the desired infusion pump unit 150A, and then press the OPTIONS hardkey 112 on the advanced interface unit 100. FIG. 20 shows the display 102 once OPTIONS hardkey 112 is pressed. The user must then press the softkey 106 corresponding to "drug calculation setup" to enter the drug calculation mode. FIG. 21 shows display 102 once the drug calculation mode is entered. In FIG. 21, display 102 illustrates the drug calculation infusion parameters to be entered during the drug calculation setup procedure. The user must enter the drug amount, diluent volume, patient weight, time units (time base to be used for the calculations), and the dosing units. To enter values for these parameters, the user must press the softkey 106 corresponding to the parameter to be entered and then use the numeric hardkeys 104 to enter the desired value.

Once the values for each parameter have been inputted, the user may press the ENTER hardkey 104 on the interface unit. FIG. 22 illustrates display 102 once ENTER hardkey 104 is pressed. The user must then enter a VTBI value and either the rate or the dose (the other value is calculated by the system and displayed). At this point, the user may begin the infusion.

As mentioned previously, a drug library containing such data as drug names, concentrations, and maximum allowable doses can be stored in the system. In a preferred embodiment of the invention, the drug calculation procedure may be used in conjunction with the drug library. To use the drug library, the user must press the "drug library" softkey 106 (shown in FIG. 21) once the drug calculation mode is entered. FIG. 23 shows display 102 containing a sample drug library. The user may use the softkeys 106 to select the appropriate drug/drug concentration from the library. This function is advantageous as the user does not have to select the correct drug amount and diluent volume for a particular drug as these values are preset in the drug library. The user then needs only to enter the patient weight (if required), VTBI, and rate or dose as described above and the drug infusion can begin.

In a preferred embodiment of the invention, the drug calculation mode may also be used to determine bolus dosing. To begin, the user simply follows the above described steps for a normal drug calculation. Once a VTBI value and either a rate or dose value is entered, the user can press the "bolus" softkey shown in FIG. 22. FIG. 24 displays the drug calculation screen for bolus dosing. The user need simply enter the desired bolus dose and duration, and the pump functional unit calculates and displays the corresponding bolus flow rate and volume to be infused as shown in FIG. 25. At this point, the user presses the START softkey and the bolus dosing begins. FIG. 26 illustrates display 102 when functional unit A is set up to deliver bolus dosing.

Finally, the system may contain a pediatric drug calculation mode (not shown) which allows the user to enter flow rate, dose, and diluent volume. From these user entered parameters, the system calculates the amount of drug to admix with the diluent to achieve a drug concentration consistent with the selected dose and flow rate.

Various embodiments of the invention have been described. The descriptions are intended to be illustrative, not limitative. Thus, it will be apparent to those skilled in the art that modifications may be made to the invention as described without departing from the scope of the claims set out below.

We claim:

1. A patient care system, comprising:
   a first interface unit including a user interface adapted to provide an interface between the system and a user of the system; and
   a functional unit capable of providing patient therapies or monitoring the condition of a patient in accordance with functional unit specific information, said functional unit removeably connected to the first interface unit and communicating therewith;
   wherein the functional unit transfers at least a portion of the functional unit specific information to the interface unit, said user interface being configured in accordance with the functional unit specific information to permit the user to execute a function of the functional unit and communicate with the first interface unit to provide external information required by the functional unit to execute said function.

2. The system of claim 1, wherein said interface unit includes a power supply and the functional unit receives its operational power requirements from the interface unit through said removable connection.

3. The system of claim 1, wherein said user interface comprises:
   a display; and
   a keyboard including a plurality of softkeys interacting with the display such that said user interface is configured in accordance with the functional unit specific information to provide predetermined command options to the user corresponding to said function.

4. The system of claim 3 further comprising a second interface unit including a user interface having a keyboard with only a plurality of function specific preprogrammed keys, wherein said functional unit is sequentially connectable to either of said first and second interface units.

5. The system of claim 3, wherein said functional unit includes a microprocessor and a resident memory containing at least a portion of said functional unit specific information and said interface unit includes a microprocessor and a resident memory containing at least a portion of said functional unit specific information.

6. The system of claim 5, wherein:
   the functional unit specific information contained in the resident memory of the functional unit includes identification means for identifying the function of the functional unit; and
   the functional unit specific information contained in the resident memory of the interface unit includes commands to configure the user interface to permit the user to execute the function of the functional unit and communicate with the first interface unit to provide external information required by the functional unit to execute said function.

7. The system of claim 6, wherein said identification means further includes means for uniquely identifying an individual functional unit.

8. The system of claim 5, wherein:
   the functional unit is an infusion pump unit;
   the functional unit specific information contained in the resident memory of the functional unit includes an identification means for uniquely identifying the functional unit and for identifying the functional unit as an infusion pump unit; and
   the functional unit specific information contained in the resident memory of the interface unit includes commands to configure the user interface to prompt the user to enter a desired infusion rate, to enter a desired volume to be infused, and to start an infusion.

9. The system of claim 8, wherein:
   the functional unit specific information contained in the resident memory of the interface unit further includes commands to configure the user interface to prompt the user to enter any one of (i) a desired drug dose, (ii) a desired flow rate and (iii) a desired bolus dose and duration; and
   the functional unit microprocessor calculates the appropriate drug dose, flow rate, or bolus rate and volume to be infused based on information entered by the user in response to said user interface prompts.

10. The system of claim 8, wherein:
    the system includes at least a first said infusion pump unit and a second said infusion pump unit, each said pump unit removeably connected to the interface unit; and
    the functional unit specific information further includes commands to configure the user interface to (i) prompt the user to enter parameters for the second pump unit after entering parameters for the first pump, and (ii) display a summary of infusion parameters entered for each said pump unit.

11. The system of claim 3, wherein said functional unit includes a microprocessor and a resident memory containing said functional unit specific information and said interface unit includes a microprocessor for configuring and controlling the user interface in accordance with said functional unit specific information contained in the resident memory of the functional unit.

12. The system of claim 11, wherein:
    the functional unit specific information contained in the resident memory of the functional unit includes an identification means for uniquely identifying the functional unit and commands to configure the user interface to permit the user to execute the function of the functional unit and communicate with the first interface unit to provide external information required by the functional unit to execute said function.

13. The system of claim 12, wherein said identification means further identifies the function of the functional unit.

14. The system of claim 11, wherein:
    the functional unit is an infusion pump unit; and
    the functional unit specific information includes commands to configure the user interface to prompt the user to enter a desired infusion rate, to enter a desired volume to be infused, and to start an infusion.

15. The system of claim 14, wherein:
    the functional unit specific information further includes commands to configure the user interface to prompt the user to enter any one of (i) a desired drug dose, (ii) a desired flow rate and (iii) a desired bolus dose and duration; and
    the functional unit microprocessor calculates the appropriate drug dose, flow rate, or bolus rate and volume to be infused based on information entered by the user in response to said user interface prompts.

16. The system of claim 14, wherein:
    the system includes at least a first said infusion pump and a second said infusion pump, each said pump removeably connected to the interface unit; and
    the functional unit specific information further includes commands to configure the user interface to (i) prompt the user to enter parameters for the second pump after entering parameters for the first pump, and (ii) display a summary of infusion parameters entered for each said pump.

17. The system of claim 1, wherein the functional unit includes a user actuatable selection key which must be actuated by the user before the user is permitted to execute a function with the functional unit.

18. The system of claim 1, wherein said functional unit comprises:
a connector to attach said functional unit to a second functional unit;
means for transferring power and communication from the interface unit to the second functional unit so that more than one functional unit is operable within the system.

19. The system of claim 18, wherein said transferring means comprises power and communication lines contained within and extending through said functional unit.

20. The system of claim 18, wherein said transferring means comprises power and communication ports on said functional unit, said ports connected by power and communication lines contained within and extending through said functional unit.

21. The system of claim 20, wherein said communication means comprises power and communication lines through said functional units.

22. The system of claim 20, wherein said first functional unit is connected to said interface unit and said second functional unit is connected to said first functional unit.

23. The system of claim 1, wherein the interface unit further comprises a communication port for the exchange of additional information with an external device.

24. The system of claim 23, wherein said additional information is an infusion protocol for facilitating infusions.

25. The system of claim 23, wherein said additional information is system configuration information for modifying the functionality of the interface unit or the functional unit.

26. The system of claim 23, wherein said additional information comprises information collected during a procedure involving said functional unit.

27. The system of claim 23, wherein said additional information comprises commands from an external unit for controlling said functional unit.

28. The system of claim 1, wherein said functional unit comprises a programmable pump unit and said functional unit specific information comprises identification of required pumping parameters including rate and volume to be infused.

29. The system of claim 28, wherein said functional unit specific information further comprises identification information for identifying the function of the functional unit.

30. The system of claim 29, wherein said identification information further comprises information for uniquely identifying the functional unit.

31. The system of claim 1, wherein the functional unit includes a user actuatable selection key which must be actuated by the user before the user is permitted to execute a function with the functional unit.

32. A patient care system, comprising:
at least one functional unit including a microprocessor and memory, said unit capable of providing patient therapies, monitoring a patient condition, or providing information to a user in accordance with functional unit specific information, wherein at least a portion of said functional unit specific information is stored in said memory; and
a first interface unit secured to and communicating with said at least one functional unit through a detachable connection to receive said functional unit specific information, said interface unit comprising a microprocessor, a resident memory, a display, a plurality of softkeys interacting with the display such that said interface is configured in accordance with said functional unit specific information to provide a functional unit specific user interface, and a power supply which supplies operational power requirements to said at least one functional unit through said detachable connection; and
wherein said functional unit specific information permits the user to execute a function of the functional unit through user manipulation of the interface unit.

33. The system of claim 32, wherein at least a portion of said functional unit specific information is stored in the resident memory of the interface unit.

34. The system of claim 33, wherein said functional unit comprises a programmable infusion pump unit and said at least a portion of said functional unit specific information stored in the resident memory of the interface unit comprises identification of required parameters for performing a patient infusion, including rate and volume to be infused.

35. The system of claim 33, wherein said at least a portion of said functional unit specific information stored in the resident memory of the interface unit comprises a redundant safety calculation capability.

36. The system of claim 32, wherein said functional unit comprises:
a connector to attach said functional unit to a second functional unit; and
means for transferring power and communication from the interface unit to the second functional unit so that more than one functional unit is operable within the system.

37. The system of claim 32, wherein the functional unit includes a user actuatable selection key which must be actuated by the user before the user is permitted to execute a function with the functional unit.

38. The system of claim 32, further comprising a first and second functional unit, wherein each said functional unit comprises a programmable pump unit and said functional unit specific information comprises identification of required pumping parameters including rate and volume to be infused.

39. A patient care system, comprising:
a first interface unit including a user interface having a first high level of interface functionality;
a second interface unit including a user interface having a second lower level of interface functionality; and
a functional unit for providing patient therapies or monitoring the condition of a patient sequentially connectable to either of said first and second interface units for receiving power and communications therefrom.

40. The system of claim 39, wherein said first interface unit further comprises:
a display; and
a keyboard including a plurality of softkeys interacting with the display so as to be configured in accordance with the functional unit specific information to provide varying command options to the user.

41. The system of claim 40 wherein said second interface unit comprises a keyboard including only a plurality of function specific preprogrammed keys, wherein said functional unit is sequentially connectable to either of said first and second interface units.

42. The system of claim 39 further comprising a plurality of functional units.

43. The system of claim 42, wherein said plurality of functional units comprises a plurality of infusion pump units.

44. The system of claim 42, wherein said plurality of functional units comprises an infusion pump unit and a blood pressure monitor unit.

45. The system of claim 42, wherein said plurality of functional units comprises an infusion pump unit and an oximeter unit.

46. The system of claim 39, wherein said functional unit comprises:
a connector to attach said functional unit to a second functional unit;
means for transferring power and information from the interface unit to the second functional unit so that more than one functional unit may be operable within the system.

47. The system of claim 39, wherein each functional unit includes a user actuatable selection key which must be actuated by the user to select a desired functional unit before the user is permitted to execute a function with the desired functional unit.

48. A method for providing care to a patient, comprising:
providing a first interface unit including an interface memory and a user interface adapted to provide an interface with a user;
attaching a functional unit to the first interface unit, wherein the functional unit is capable of providing patient therapies or monitoring the condition of the patient in accordance with functional unit specific information;
transferring at least a portion of the functional unit specific information from the functional unit to the first interface unit;
configuring said user interface in accordance with the functional unit specific information to provide a user interface for said functional unit;
manipulating the user interface to set up the functional unit to perform a desired function; and
performing the desired function with the functional unit.

49. The method of claim 48, further comprising the step of storing the functional unit specific information in a functional unit memory.

50. The method of claim 49, wherein the functional unit specific information stored in the functional memory includes commands to configure the user interface to permit the user to execute the function of the functional unit and communicate with the first interface unit to provide external information required by the functional unit to execute said function.

51. The method of claim 50, wherein the functional unit specific information stored in the functional memory further includes an identification means for uniquely identifying the functional unit.

52. The method of claim 48, further comprising the step of storing a portion of the functional unit specific information in the interface memory.

53. The method of claim 52, wherein said portion of the functional unit specific information in the interface memory includes commands to configure the user interface to permit the user to execute the function of the functional unit and communicate with the first interface unit to provide external information required by the functional unit to execute said function.

54. The method of claim 53, wherein the portion of functional unit specific information in the functional memory includes an identification means for uniquely identifying the functional unit.

55. The method of claim 48, further comprising:
attaching at least two functional units to the first interface unit; and
selecting one said functional unit to perform the desired function, wherein said selecting includes the step of the user physically touching the selected functional unit prior to performance of the desired function.

56. The method of claim 48, wherein said step of manipulating the user interface comprises inputting data and entering commands required by the functional unit, through said user interface, for the performance of the desired function.

57. The method of claim 56, wherein desired function is a fluid infusion.

58. The method of claim 56, wherein the desired function is monitoring patient electrocardiographic status.

59. The method of claim 56, wherein the desired function is monitoring patient blood pressure.

60. The method of claim 56, wherein said step of inputting data and entering commands is accomplished at least in part through a communication port connected to the interface unit for the exchange of information with an external device.

61. The method of claim 60, wherein the information is an infusion protocol for facilitating infusions.

62. The method of claim 60, wherein the information is system configuration information for modifying the functionality of the interface unit or the functional unit.

63. The method of claim 60, wherein the information is information collected during a procedure involving said functional unit.

64. The method of claim 60, wherein the information is commands from an external unit for controlling said units.

65. A method for controlling the infusion of fluids to a patient from a plurality of pump units, comprising:
providing an interface unit including a user interface adapted to provide an interface with a user;
attaching a plurality of pump units to the interface unit, wherein each pump unit is capable of performing fluid infusion to a patient in accordance with pump unit specific information;
transferring at least a portion of the pump unit specific information from each pump unit to the interface unit;
configuring said user interface in accordance with each said pump unit specific information to selectively provide a user interface for each of said pump units;
manipulating the user interface to set up each pump unit so as to perform an infusion in accordance with a predetermined infusion protocol; and
performing an infusion according to the predetermined infusion protocol with the plurality of pump units.

66. The method of claim 65, further comprising the step of storing each said pump unit specific information in a memory of each said pump unit.

67. The method of claim 66, wherein each said pump unit specific information in the memory of each said pump unit includes commands to configure the user interface to prompt the user to enter a desired infusion rate, to enter a desired volume to be infused, and to start an infusion.

68. The method of claim 65, further comprising the step of storing at least a portion of each said pump unit specific information in a memory of the interface unit.

69. The method of claim 68, wherein each said pump unit specific information in the memory of the interface unit includes commands to configure the user interface to prompt the user to enter a desired infusion rate, to enter a desired volume to be infused, and to start an infusion.

70. The method of claim 68, wherein said pump unit specific information in the memory of the interface unit includes a redundant safety calculation capability.

71. The method of claim 65, wherein the step of manipulating further comprises:

prompting the user to enter values for rate and volume to be infused; and entering said values such that each pump unit performs in accordance with the predetermined infusion protocol.

72. The method of claim 65, wherein the predetermined infusion protocol is provided to the system using a data storage card receptacle on the interface unit.

73. The method of claim 72, further comprising:

providing a data storage card;

storing the predetermined multiple unit infusion protocol on the data storage card;

transferring the predetermined multiple unit infusion protocol to the system by engaging said data storage card in electronic communication with said data storage card receptacle; and executing commands to the interface unit to transfer said protocol.

74. A method for providing care to a patient, comprising:

providing a first interface unit including a user interface having a first high level of functionality;

removeably connecting a functional unit for providing patient therapies or monitoring the condition of a patient to the first interface unit, wherein the functional unit receives power and communications from the first interface unit; and interchanging a second interface unit including a user interface having a second lower level of functionality with the first interface unit when predetermined requirements change.

75. The method of claim 74, wherein said first interface unit further comprises:

a display; and a keyboard including a plurality of softkeys interacting with the display so as to be configured in accordance with the functional unit specific information to provide varying command options to the user.

76. The method of claim 75, wherein said second interface unit comprises a keyboard including only a plurality of function specific preprogrammed keys, wherein said functional unit is sequentially connectable to either of said first and second interface units.

77. The method of claim 74, further comprising the step of providing a plurality of functional units for connection to said interface units.

78. A patient care system, comprising:

an interface unit adapted to provide an interface between the system and a user of the system; and at least first and second functional units, each capable of providing patient therapies or monitoring the condition of a patient in accordance with functional unit specific information;

wherein each said functional unit includes communication means for communicating with the interface unit and for providing communication between another functional unit and the interface unit such that said functional units may be secured to and supported by one another in any arrangement and order while communicating with the interface unit.

* * * * *